United States Patent
Owens et al.

(10) Patent No.: US 8,784,499 B2
(45) Date of Patent: Jul. 22, 2014

(54) PREPARATION OF REGENERATIVE TISSUE SCAFFOLDS

(75) Inventors: Rick Owens, Stewartsville, NJ (US); Wendell Sun, Warrington, PA (US); Mike Liu, Hillsborough, NJ (US); Yong Mao, Basking Ridge, NJ (US)

(73) Assignee: LifeCell Corporation, Branchburg, NJ (US)

( * ) Notice: Subject to any disclaimer, the term of this patent is extended or adjusted under 35 U.S.C. 154(b) by 112 days.

(21) Appl. No.: 13/070,891

(22) Filed: Mar. 24, 2011

(65) Prior Publication Data
US 2011/0238186 A1    Sep. 29, 2011

Related U.S. Application Data

(60) Provisional application No. 61/317,443, filed on Mar. 25, 2010.

(51) Int. Cl.
*A61F 2/28* (2006.01)
(52) U.S. Cl.
USPC ............ 623/23.57; 623/11.11; 623/23.59
(58) Field of Classification Search
CPC ...... A61F 2/34; A61F 2/30767; A61F 2/3094
USPC ................. 623/11.11, 23.57–23.59
See application file for complete search history.

(56) References Cited

U.S. PATENT DOCUMENTS

| | | |
|---|---|---|
| 5,284,655 A | 2/1994 | Bogdansky et al. |
| 5,290,558 A | 3/1994 | O'Leary et al. |
| 5,336,616 A | 8/1994 | Livesey et al. |
| 5,584,801 A | 12/1996 | Kuroyanagi et al. |
| 6,189,537 B1 | 2/2001 | Wolfinbarger et al. |
| 6,305,379 B1 | 10/2001 | Wolfinbarger et al. |
| 6,933,326 B1 | 8/2005 | Griffey et al. |
| 7,358,284 B2 | 4/2008 | Griffey et al. |
| 7,498,040 B2 | 3/2009 | Masinaei et al. |
| 7,498,041 B2 | 3/2009 | Masinaei et al. |
| 2002/0082685 A1* | 6/2002 | Sirhan et al. ............ 623/1.42 |
| 2002/0082697 A1 | 6/2002 | Damien |
| 2003/0009235 A1 | 1/2003 | Manrique et al. |
| 2003/0035843 A1 | 2/2003 | Livesey et al. |
| 2003/0143207 A1 | 7/2003 | Livesey et al. |

(Continued)

FOREIGN PATENT DOCUMENTS

| | | |
|---|---|---|
| EP | 1127581 A1 | 8/2001 |
| WO | WO 03/017826 | 3/2003 |

(Continued)

OTHER PUBLICATIONS

International Search Report and Written Opinion for PCT/US2011/029751 mailed Jun. 9, 2011, from the International Searching Authority of the European Patent Office.

(Continued)

*Primary Examiner* — Jason-Dennis Stewart
(74) *Attorney, Agent, or Firm* — McCarter & English, LLP; Matthew R. Van Eman

(57) ABSTRACT

Devices and methods for treating or repairing a tissue or organ defect or injury are provided. The devices can include tissue scaffolds produced from acellular tissue matrices and polymers, which have a stable three-dimensional shape and elicit a limited immunologic or inflammatory response.

23 Claims, 11 Drawing Sheets

(56) References Cited

U.S. PATENT DOCUMENTS

| | | |
|---|---|---|
| 2005/0028228 A1* | 2/2005 | McQuillan et al. ............ 800/17 |
| 2005/0069573 A1* | 3/2005 | Cohn et al. .................... 424/426 |
| 2005/0113938 A1 | 5/2005 | Jamiolkowski et al. |
| 2005/0125077 A1 | 6/2005 | Harmon et al. |
| 2005/0288796 A1 | 12/2005 | Awad et al. |
| 2006/0073592 A1 | 4/2006 | Sun et al. |
| 2006/0127375 A1 | 6/2006 | Livesey et al. |
| 2006/0210960 A1 | 9/2006 | Livesey et al. |
| 2006/0216321 A1 | 9/2006 | Lyu et al. |
| 2007/0082058 A1 | 4/2007 | Masinaei et al. |
| 2007/0248575 A1 | 10/2007 | Connor et al. |
| 2008/0027542 A1 | 1/2008 | McQuillan et al. |
| 2009/0035289 A1 | 2/2009 | Wagner et al. |
| 2009/0306790 A1 | 12/2009 | Sun |
| 2010/0036503 A1 | 2/2010 | Chen et al. |
| 2010/0040687 A1* | 2/2010 | Pedrozo et al. ............... 424/484 |
| 2010/0137677 A1 | 6/2010 | Friedman et al. |
| 2010/0161054 A1 | 6/2010 | Park et al. |
| 2010/0209408 A1 | 8/2010 | Stephen et al. |
| 2010/0272782 A1 | 10/2010 | Owens et al. |
| 2011/0002996 A1 | 1/2011 | McQuillan et al. |
| 2011/0004306 A1 | 1/2011 | Harper |
| 2011/0022171 A1 | 1/2011 | Richter et al. |
| 2011/0044847 A1 | 2/2011 | Kibalo |
| 2011/0054588 A1 | 3/2011 | Xu et al. |
| 2011/0135706 A1 | 6/2011 | Xu et al. |
| 2011/0208320 A1 | 8/2011 | Stevenson et al. |

FOREIGN PATENT DOCUMENTS

| | | |
|---|---|---|
| WO | WO-2004/014452 A2 | 2/2004 |
| WO | WO 2004/069296 | 8/2004 |
| WO | WO 2007/134134 | 11/2007 |
| WO | WO-2011/031637 A2 | 3/2011 |

OTHER PUBLICATIONS

Han et al., "Effects of moisture and temperature on the osteoinductivity of demineralized bone matrix," J. Orthop Res 23:855-861 (2005).

Han et al., "Effects of Gamma Irradiation on Osteoinduction Associated with Demineralized Bone Matrix," J. Orthop Res. 26(1):75-82 (2008).

Suckow et al., "Enhanced Bone Regeneration Using Porcine Small Intestinal Submucosa," J. Invest Surg 12:277-287 (1999).

Qiu et al., "Evaluation of Bone Regeneration at Critical-Sized Calvarial Defect by DBM/AM Composite," J. Biomed Mater Res B Appl Biomater 81(2):516-523 (2007).

* cited by examiner

PREPARATION OF REGENERATIVE TISSUE SCAFFOLDS

This application claims priority to U.S. Provisional Patent Application No. 61/317,443, which was filed on Mar. 25, 2010.

The present disclosure relates to devices and methods for treating tissue or organ defects or injuries, including tissue scaffolds for treating tissue defects.

Human, animal, and synthetic materials are currently used in medical and surgical procedures to augment tissue or repair or correct tissue defects. For certain purposes, materials with stable preformed shapes are needed. For example, for certain bone defects and soft tissue defects, stable three-dimensional structured devices are required to correspond with the defect site and allow regeneration of tissue with a desired structure. However, various devices and methods for repairing or correcting tissue or organ defects have had certain disadvantages.

Accordingly, there is a need for improved devices with better stability for medical applications.

In certain embodiments, a method for making a tissue scaffold is provided. The method comprises dissolving a polymer in a solvent to make a solution; mixing the solution with a particulate acellular tissue matrix (ATM) to create a mixture; placing the mixture in a mold; drying the mixture to form a tissue scaffold with a stable three-dimensional shape, wherein the tissue scaffold has a reduced immunological or inflammatory response when implanted in a human than the polymer alone.

In certain embodiments, a tissue scaffold is provided. The tissue scaffold comprises a particulate ATM and a polymer, wherein the ATM is encased in the polymer to form a stable three-dimensional tissue scaffold for tissue regeneration, and wherein the tissue scaffold has a reduced immunological or inflammatory response when implanted in a human than the polymer alone In certain embodiments, a method of treating a tissue defect is provided. The method comprises selecting a tissue scaffold having a stable three-dimensional shape, the scaffold comprising a particulate ATM; and a polymer, wherein the ATM is encased in the polymer to form a stable three-dimensional tissue scaffold for tissue regeneration; identifying a defect in a tissue or organ; and implanting the tissue scaffold in the defect.

DESCRIPTION OF EXEMPLARY EMBODIMENTS

Figure 1:
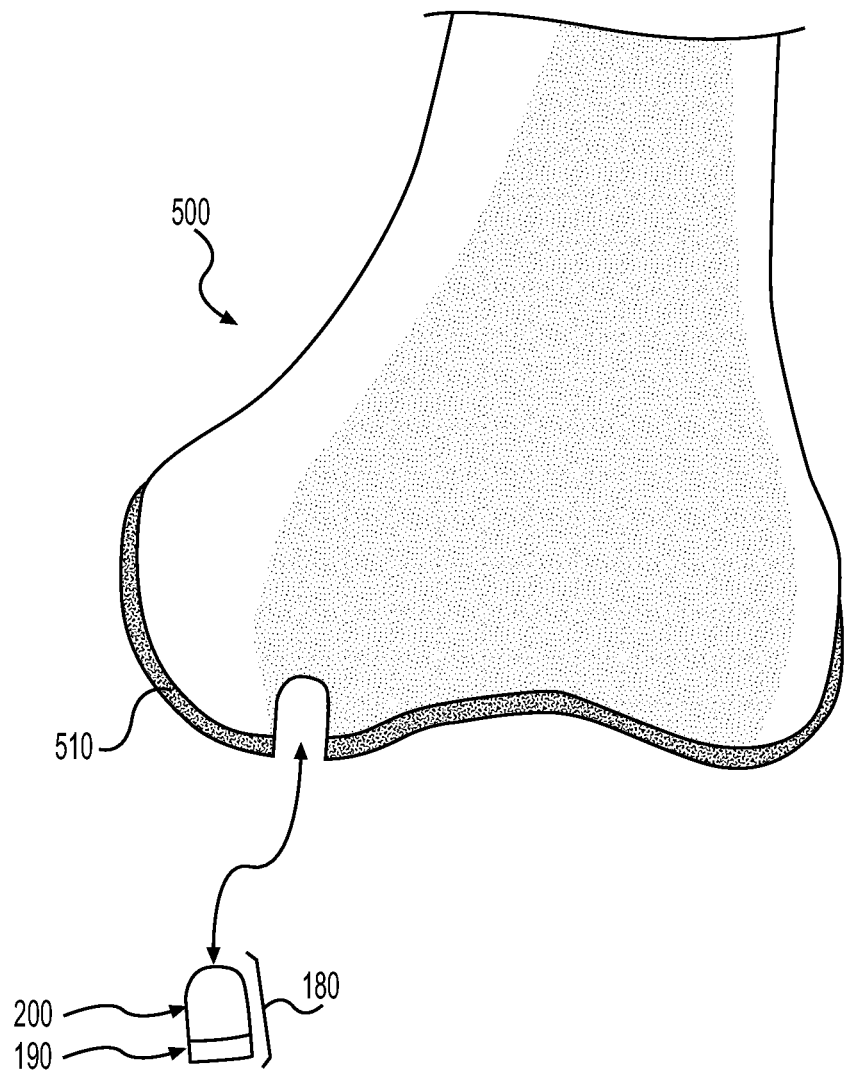
FIG. 1 illustrates implantation of a tissue scaffold in a defect, according to certain embodiments.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "acellular tissue matrix," as used herein, refers generally to any tissue matrix that is substantially free of cells and/or cellular components. Skin, parts of skin (e.g., dermis), and other tissues such as blood vessels, heart valves, fascia, cartilage, bone, and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components. For example, DNA or other nucleic acid assays can be used to quantify remaining nuclear materials within the tissue matrices. Generally, the absence of remaining DNA or other nucleic acids will be indicative of complete decellularization (i.e., removal of cells and/or cellular components). Finally, other assays that identify cell-specific components (e.g., surface antigens) can be used to determine if the tissue matrices are acellular.

The present disclosure provides three-dimensional tissue scaffolds to treat defects in tissues or organs. The tissue scaffolds can include an ATM that has the biologic ability to support tissue regeneration. In some embodiments, tissue scaffolds can support cell ingrowth and differentiation. For example, the scaffolds can be used for tissue ingrowth, orthopedic surgery, periodontal applications, tissue remodeling, tissue restoration, plastic surgery, cosmetic surgery, and replacement of lost tissue, for example to lumpectomy, parotidectomy, or excision of tumors, as described further below.

In addition, the tissue scaffolds can include one or more polymeric materials, as described further below. In certain embodiments, the tissue scaffolds of the present disclosure can increase the acceptance of the polymeric component via attenuation or reduction of immunological or inflammatory response. As used herein, the polymeric components can include synthetic polymers and/or naturally occurring polymers. In certain embodiments, the polymeric materials in the tissue scaffolds can provide a stable three-dimensional structure to the ATM, which increases implant integration and biocompatibility. As used herein, the stable three-dimensional structure will be understood to refer to a material that tends to maintain a predetermined shape (e.g. formed to conform to an implant site) when in a resting state.

In various embodiments, tissue scaffolds of the present disclosure can be used for treatment at numerous different anatomical sites. According to various embodiments, tissue scaffolds can be used in a wide array of applications. Certain exemplary applications include, but are not limited to, absorptive dressing, dermal regeneration (for example, for treatments of all types of ulcers and burns), nerve regeneration, cartilage regeneration, connective tissue regeneration or repair (for example, tendon/ligament sleeve), bone regeneration, periodontal applications, wound/foam lining, integrated bandage dressing, substrate/base for skin grafts, vascular regeneration, cosmetic surgery, metal and/or polymer implant coating (for example, to increase implant integration and biocompatibility), and replacement of lost tissue (e.g., after trauma, breast reduction, mastectomy, lumpectomy, parotidectomy, or excision of tumors).

In some embodiments, the tissue scaffold elicits a reduced immunological or inflammatory response when implanted in a human compared to than the polymer or polymers used to produce the scaffold alone. In some embodiments, the effect of the tissue scaffold in the host can be tested using a number of methods. In some embodiments, the effect of the tissue scaffold in the host can be tested by measuring immunological or inflammatory response to the implanted scaffold. In some embodiments, the immunological or inflammatory response to the tissue scaffold can be measured by a number of methods. In some embodiments, the immunological or inflammatory response can be measured using histological methods. For example, explanted scaffold can be stained, and observed under microscope for histological evaluation, as described further below. In some embodiments, the immunological or inflammatory response to the scaffold can be demonstrated by measuring the number of inflammatory cells (e.g., leukocytes). In some embodiments, the attenuated immunological or inflammatory response to the scaffold can be demonstrated by a reduced number of inflammatory cells, as described further below. For example, inflammatory cells can be measured through immuno-histochemical staining methods designed to identify lymphocytes, macrophages and neutrophils. Immuno-histochemical methods may also be used to determine the presence of inflammatory cytokines including interleulin-1, TNF-alpha, and TGF-beta.

In various embodiments, tissue scaffolds of the present disclosure can be used to treat any of a wide range of disorders. Tissue defects can arise from diverse medical conditions, including, for example, congenital malformations, traumatic injuries, infections, and oncologic resections. Thus, the tissue scaffolds can be used to repair defects in any soft tissue, e.g., tissues that connect, support, or surround other structures and organs of the body. The tissue scaffolds can also be used to treat bone defects, e.g., as an articular graft to support cartilage regeneration. Soft tissue can be any non-osseous tissue.

The tissue scaffolds can be used to treat soft tissues in many different organ systems. These organ systems can include, but are not limited to, the muscular system, the genitourinary system, the gastroenterological system, the integumentary system, the circulatory system, and the respiratory system. The tissue scaffolds are also useful to treat connective tissue, including the fascia, a specialized layer that surrounds muscles, bones and joints, of the chest and abdominal wall and for repair and reinforcement of tissue weaknesses in urological, gynecological and gastroenterological anatomy.

In another embodiment, the tissue or organ defect is selected from the group consisting of skin, bone, cartilage, meniscus, dermis, myocardium, periosteum, artery, vein, stomach, small intestine, large intestine, diaphragm, tendon, ligament, neural tissue, striated muscle, smooth muscle, bladder, urethra, ureter, and gingival.

For example, FIG. 1 illustrates implantation of a tissue scaffold in a cartilage defect, according to certain embodiments. As shown, a tissue scaffold 180 can be used to treat a cartilage defect in a long bone 500 (e.g., femur or humerus). In various embodiments, a scaffold 180 can be used to treat an articular surface or cartilage 510 of any joint. In various embodiments, the tissue scaffold 180 can be placed in a defect or excised area of an articular surface or cartilage 510.

In some embodiments, the tissue scaffold 180 comprises an ATM and a polymer. In some embodiments, the ATM comprises tissues from two different tissue sources, for example, cartilage 190 and demineralized bone 200. In some embodiments, the tissue scaffold 180 can be used to repair other tissue or organ defects. In some embodiments, the tissue scaffold 180 can comprise dermis and cartilage. In some embodiments, the tissue scaffold comprises cartilage 190 without demineralized bone 200. In some embodiments, the tissue scaffold 180 can comprise demineralized bone 200 without cartilage 190. In some embodiments, the tissue scaffold 180 can comprise dermis.

In certain embodiments, a method of making a tissue scaffold comprises dissolving a polymer in a solution; mixing the solution with a particulate ATM to form a mixture; and molding and shaping the tissue scaffold to a stable three-dimensional structure by removing the solvent.

Figure 2:
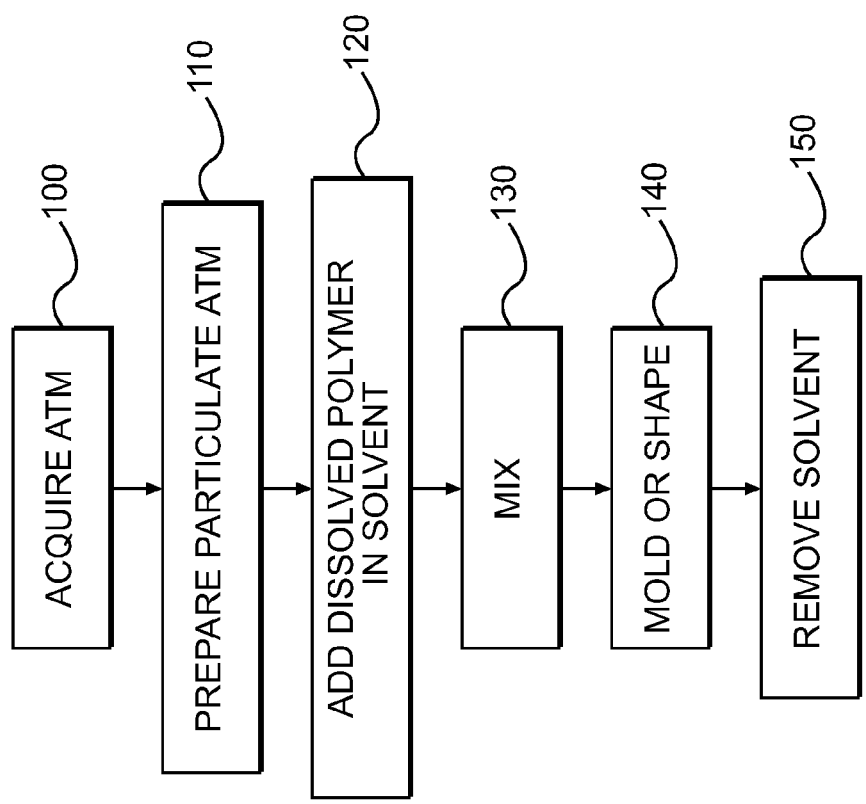
FIG. 2 is a flow chart showing a process for producing a tissue scaffold, according to certain embodiments.

FIG. 2 illustrates preparation of a three-dimensional tissue scaffold. The scaffolds can include an ATM (step 100). In some embodiments the ATM can be derived from, for example, dermis, cartilage, bone, demineralized bone, blood vessels, heart valves, fascia, or nerve connective tissue. In some embodiments, the particulate ATM comprises uniform size particles. In some embodiments, the particulate ATM comprises a dermal ATM. In some embodiments, the dermal ATM is a human tissue matrix. In some embodiments, the dermal ATM is a porcine tissue matrix. In some embodiments, the particulate ATM is a cartilage tissue matrix, which may be derived from human cartilage. In some embodiments, the cartilage tissue matrix is derived from porcine cartilage. In some embodiments, the particulate ATM comprises a bone tissue matrix. In some embodiments, the bone tissue matrix is derived from human bone. In some embodiments, the bone tissue matrix is derived from porcine bone.

The ATM can be selected to provide a variety of different biologic and mechanical properties. For example, the ATM can be selected to allow tissue ingrowth and remodeling to allow regeneration of tissue normally found at the site where the matrix is implanted. For example, the ATM, when implanted on or into cartilage, may be selected to allow regeneration of the cartilage without excessive fibrosis or scar formation. In addition, the ATM should not elicit an excessive inflammatory reaction, and should ultimately be remodeled to produce tissue similar to the original host tissue. In some embodiments, the ATM comprises collagen, elastin, and vascular channels. In certain embodiments, the ATM can include ALLODERM® or Strattice™, which are human and porcine acellular dermal matrices respectively. Examples of such materials may be found in U.S. Pat. Nos. 6,933,326 and 7,358,284. Alternatively, other suitable acellular tissue matrices can be used, as described further below.

A particulate ATM can be prepared by cryomilling ATM (step 110). The particulate ATM can be derived from many different tissue sources. The tissue sources can be, for example, dermis, cartilage, bone blood vessels, heart valves, fascia, and nerve connective tissue. They are described in detail below. In some embodiments, two or more different types of tissues can be used to prepare particulate ATM.

In addition, the tissue scaffolds can include one or more polymeric materials. In some embodiments, the polymeric materials can be selected from a number of polymers. In certain embodiments, the polymers can be selected, for example, from chitosan, benzyl ester of hyaluronic acid (BHA), polycaprolactone (PCL), or poly-4-hydroxybutyrate (P4HB). In some embodiments, the polymer can be dissolved in a suitable solvent selected from a number of solvents (step 120). In some embodiments, the solvent can be selected, for example, from dioxane, N-methyl-2-pyrrolidone (NMP), DMSO, or acetic acid. In one embodiment, the PCL is dissolved in dioxane. In another embodiment, the PCL in dioxane or NMP solvent used in the preparation of tissue scaffold can be about 5-30% (w/v). In a further embodiment, the PCL in dioxane or NMP solvent used in the preparation of tissue scaffold can be 5%, 8%, 10%, 12%, 15%, 18%, 20%, 25%, or 30% (w/v), 5% to 30% (w/v), 10% to 30% (w/v) and any values in between. In another embodiment, the P4HB is dissolved in dioxane or NMP. In yet another embodiment, the P4HB in dioxane or NMP solvent used in the preparation of tissue scaffold can be about 5-40% (w/v). In a further embodiment, the P4HB in dioxane or NMP solvent used in the preparation of tissue scaffold can be 5%, 8%, 10%, 12%, 15%, 18%, 20%, 25%, 30%, or 40% (w/v), or 5% to 40% (w/v), 10% to 30% (w/v) and any values in between. In another embodiment, the BHA is dissolved in DMSO. In yet another embodiment, the BHA in DMSO used in the preparation of tissue scaffold can be about 5-50% (w/v). In a further embodiment, the BHA in DMSO used in the preparation of tissue scaffold can be 5%, 8%, 10%, 12%, 15%, 18%, 20%, 25%, 30%, 40%, or 50% (w/v), 5% to 50% (w/v), or 10% to 40% (w/v), and any values in between. In yet another embodiment, the chitosan is dissolved in acetic acid. In a further embodiment, the acetic acid concentration is 0.1-0.5 M (pH range 2.53-2.88). In a further embodiment, the pH of the chitosan and acetic acid mixture can be 4.0-5.5. In yet another embodiment, the chitosan in acetic acid used in the preparation of tissue scaffold can be 1%, 2%, 3%, 4%, or 5% (w/v), and any values in between. Each of these scaffold materials may impart different properties upon the final product allowing for the manipulations of in vivo turnover/persistence, biomechanical properties, and overall biological response.

The polymer solution can be mixed with the particulate ATM (step 130). The ATM and polymer/solvent mixtures can be placed or packed into molds (step 140). In some embodiments, molds can be selected from a number of molds. In some embodiments, the molds can be selected from eppendorf tube, metal tube, injection tube, or a mold in the form of a tissue or organ defect for which the tissue scaffold is designed to repair.

The solvent can be removed through a drying process (step 150). In some embodiments, the solvent can be removing through a number of drying processes. In some embodiments, the drying processes can be selected from freeze drying, air drying, heated drying, drying in an argon or nitrogen atmosphere, or vacuum assisted drying. The resulting tissue scaffolds consist of regenerative tissue particles encased in a polymeric/synthetic support scaffold and are stable under mechanical stress. In addition, the drying process can include passive drying, wherein the solvent evaporates into a normal atmosphere.

In certain embodiments, shape and stability of the tissue scaffold are important. In some embodiments, the desired or performed shape and size of the resulting tissue scaffold is determined by the shape and size of a mold used to produce the scaffold. In some embodiments, the desired or performed shape of the tissue scaffold is a stable three-dimensional shape. In some embodiments, the mold used to prepare the stable three-dimensional tissue scaffold can be an eppendorf tube, a metal tube, an injection tube, or a mold in the form of a tissue or organ defect in which the tissue scaffold will be implanted. In some embodiments, the tissue scaffold is in a cylindrical shape. In some embodiments, the tissue scaffold is in a tubular shape. In some embodiments, the shape of the tissue scaffold corresponds to the shape of the tissue or organ defect or injury. In some embodiments, mechanical strength, porosity, hydration and fluid conductance are controlled by controlling freezing rate, freezing temperature, and the composition of the molding container.

In some embodiments, the tissue scaffold is sized or shaped such that it can correspond to the shape of the tissue or organ defect. In some embodiments, the tissue scaffold can be prepared using two or more different types of tissues. For example, one of the tissues in the tissue scaffold can be cartilage and the second tissue can be demineralized bone. In some embodiments, cartilage/demineralized bone scaffold can be used to repair osteochondral defects (FIG. 1).

Acellular Tissue Matrices

The term "acellular tissue matrix," as used herein, refers generally to any tissue matrix that is substantially free of cells and/or cellular components. Skin, parts of skin (e.g., dermis), and other tissues such as blood vessels, heart valves, fascia, cartilage, bone, and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components. For example, DNA or other nucleic acid assays can be used to quantify remaining nuclear materials within the tissue matrices. Generally, the absence of remaining DNA or other nucleic acids will be indicative of complete decellularization (i.e., removal of cells and/or cellular components). Finally, other assays that identify cell-specific components (e.g., surface antigens) can be used to determine if the tissue matrices are acellular. Skin, parts of skin (e.g., dermis), and other tissues such as blood vessels, heart valves, fascia, cartilage, bone, and nerve connective tissue may be used to create acellular matrices within the scope of the present disclosure.

In general, the steps involved in the production of an ATM include harvesting the tissue from a donor (e.g., a human cadaver or animal source) and cell removal under conditions that preserve biological and structural function. For example, desired biologic and structural functions include the ability to support cell ingrowth and tissue regeneration, to provide mechanical support (e.g., to a surgical site or defect), to prevent excessive immunologic response, inflammation, fibrosis, and/or scarring. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The integrity of the collagen matrix can be tested in a number of ways. For example, differential scanning calorimetry can be used to identify changes in thermal transition temperature that indicate crosslinking (elevation in transition temperature) or collagen degredation (decrease in transition temperatures). In addition, electron microscopy can demonstrate changes in normal collagen patterns, and enzymatic digestion assays can demonstrate collagen damage. Further, the loss of various glycosaminoglycans (e.g., chondroitin sulfate and hyaluronic acid) can indicate an undesirable change in the tissue matrix.

The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent crosslinking, one or more protease inhibitors, and/or one or more enzymes. Suitable methods for producing ATM are described, for example, H. Xu et al., A Porcine-Derived Acellular Dermal Scaffold That Supports Soft Tissue Regeneration: Removal of Terminal Galactose-$\alpha$-(1,3)-Galactose and Retention of Matrix Structure. Tissue Eng. Part A 15: 1807 (2009).

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable buffer can be used as long as the buffer provides suitable DNase activity.

While an ATM may be made from one or more individuals of the same species as the recipient of the tissue scaffold, this is not necessarily the case. Thus, for example, an ATM in the tissue scaffold may be made from porcine tissue. Species that can serve as recipients of ATM and donors of tissues or organs for the production of the ATM include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) on macromolecules such as glycoproteins of the extracellular components. U. Galili et al., J. Biol. Chem. 263: 17755 (1988). This epitope is absent in Old World primates (monkeys of Asia and Africa and apes) and humans, however. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of collagen-containing material from these mammals into primates often results in rejection because of primate anti-Gal binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896,594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

After the ATM is formed, histocompatible, viable cells may optionally be seeded in the ATM to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the ATM or by infusing or injecting cells obtained from the recipient or histocompatible cells from another donor into the ATM in situ. Various cell types can be used, including embryonic stem cells, adult stem cells (e.g. mesenchymal stem cells), and/or neuronal cells. In various embodiments, the cells can be directly applied to the inner portion of the ATM just before or after implantation. In certain embodiments, the cells can be placed within the ATM to be implanted, and cultured prior to implantation. In one embodiment, viable cells are added to the tissue scaffold prior to implantation. In one embodiment, viable cells are added to the tissue scaffold after the scaffold is implanted at a desired anatomic site.

Particulate Acellular Tissue Matrix

The following procedure can be used to produce particulate acellular tissue matrices using ALLODERM®, STRATTICE™ LifeCell Corporation, Branchburg, N.J., or other suitable acellular tissue matrices. After removal from the packaging, ATM is cut into strips using a Zimmer mesher fitted with a non-interrupting "continuous" cutting wheel. The resulting long strips of ATM are cut into lengths of about 1 to about 2 centimeters in length.

A homogenizer and sterilized homogenizer probe, such as a LabTeck Macro homogenizer available from OMNI International, Warrenton Va., is assembled and cooled to cryogenic temperatures using sterile liquid nitrogen which is poured into the homogenizer tower. Once the homogenizer has reached cryogenic temperatures, ATM previously prepared into strips as noted above are added to the homogenizing tower containing sterile liquid nitrogen. The homogenizer is then activated so as to cryogenically fracture the strips of ATM. The time and duration of the cryogenic fractionation step will depend upon the homogenizer utilized, the size of the homogenizing chamber, the speed and time at which the homogenizer is operated and should be able to be determined by one of skill in the art by simple variation of the parameters to achieve the desired results.

The cryofractured particulate ATM material is sorted by particle size by washing the product of the homogenizer with liquid nitrogen through a series of metal screens that have also been cooled to liquid nitrogen temperatures. We have found it especially useful to utilize a combination of screens within the homogenizing tower of the type described above in which the particles are washed and sorted first to exclude oversized particles and then to exclude undersized particles.

Once isolated, the particulate ATM is removed and placed in a vial for freeze drying once the sterile liquid nitrogen has evaporated. This last step is to ensure that any residual moisture that may have been absorbed during the above procedure is removed.

The final product can be a powder having a particle size of about 1 micron to about 900 microns or a particle size of about 30 microns to about 750 microns. The particles are distributed about a mean of about 150-300 microns. The material is readily rehydrated by suspension in normal saline or other similar suitable rehydrating agent. The rehydrated ATM may be resuspended in normal saline or any other suitable pharmaceutically compatible carrier.

The following examples are provided to better explain the various embodiments and should not be interpreted in any way to limit the scope of the present disclosure.

EXAMPLES

Example 1

Preparation of Regenerative Tissue Scaffold

FIG. 2 illustrates a process of preparation of synthetic ATM regenerative tissue scaffold. Three dimensional regenerative tissue scaffolds were created from particulate ATM using polymeric scaffold materials. ATM was prepared from porcine dermal tissue and freeze dried. Dry ATM was cut into ~1 cm$^2$ pieces and placed into an appropriate size cryomill vial. The vial was then placed in a SPEX 6800 freezer mill that has been pre-cooled with liquid nitrogen and subjected to a cryofracture protocol. The particulate ATM was then removed from the vial and maintained under dry storage conditions.

A 100% benzyl ester derivative of hyaluronic acid was solubilized in dimethyl sulfoxide (DMSO) at a concentration of 40% (w/v). One ml of this solution was then mixed with 300 mg of particulate acellular dermal matrix, as prepared above, and the mixture was transferred to a small 2 ml eppendorf tube. The DMSO was then removed through a freeze dry process leaving a tissue scaffold (40% benzyl ester hyaluronic acid, 60% acellular dermal matrix by weight) that retained the form of the eppendorf tube (cylindrical) it was dried in (step 150).

Example 2

Functional Study of Tissue Scaffold

Calorimetric Analysis of Effect of Organic Solvents on Tissue Matrix Integrity

Figure 3:
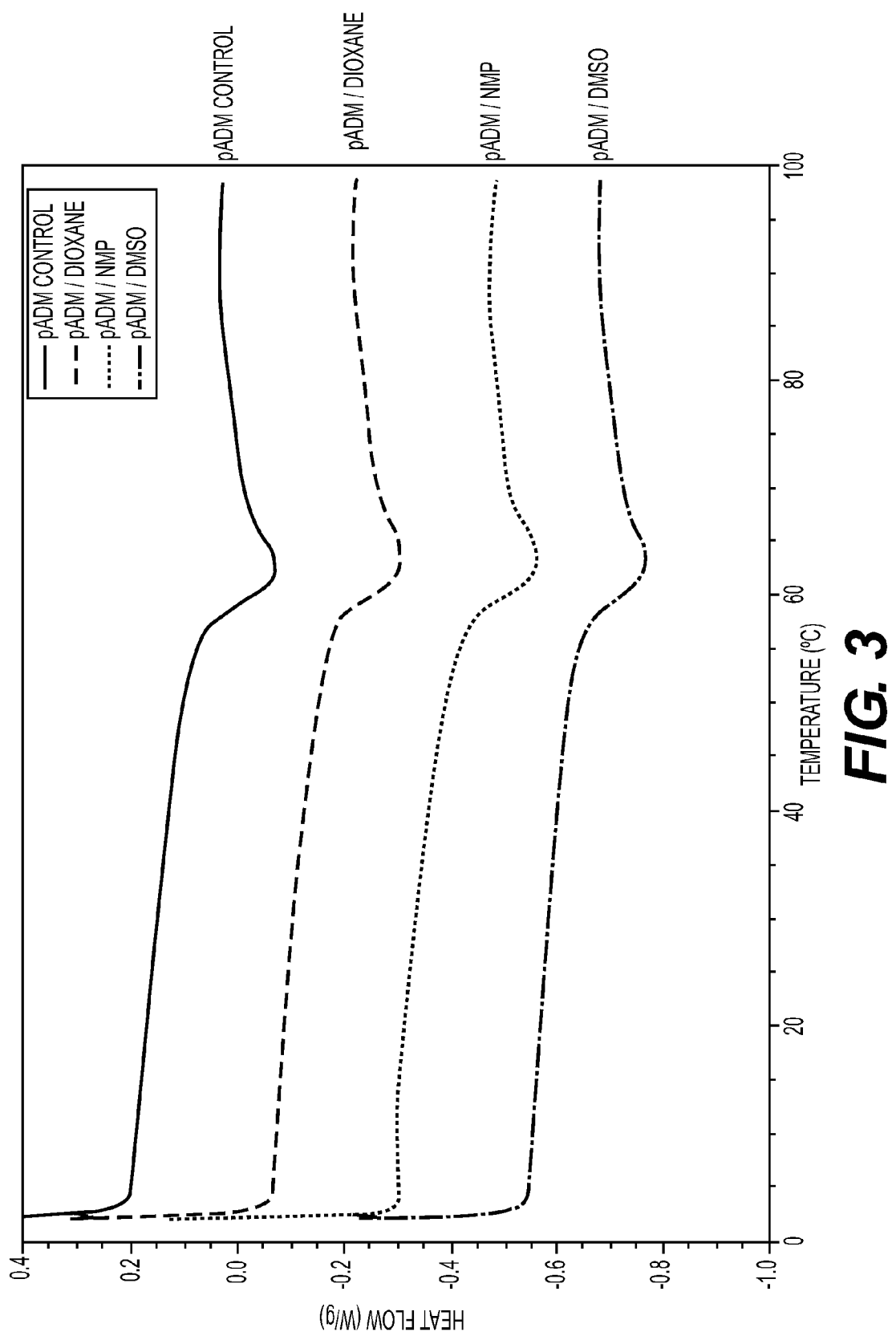
FIG. 3 is a graph of differential scanning calorimetry (DSC) data of porcine acellular dermal matrix (pADM) treated with organic solvents, according to Example 2.

In vivo results suggested that the presence of the regenerative tissue matrix attenuates the immunological or inflammatory response to the scaffold material as demonstrated by reduced number of inflammatory cells.

pADMs, prepared as described in Example 1, were treated with an excess of different solvents including dioxane, NMP, and DMSO, for 2 hr. The treated materials were evaluated with differential scanning calorimeter (DSC) to assess tissue matrix integrity. FIG. 3 is a graph of DSC data of porcine acellular dermal matrix (pADM) treated with organic solvents.

Figure 4:
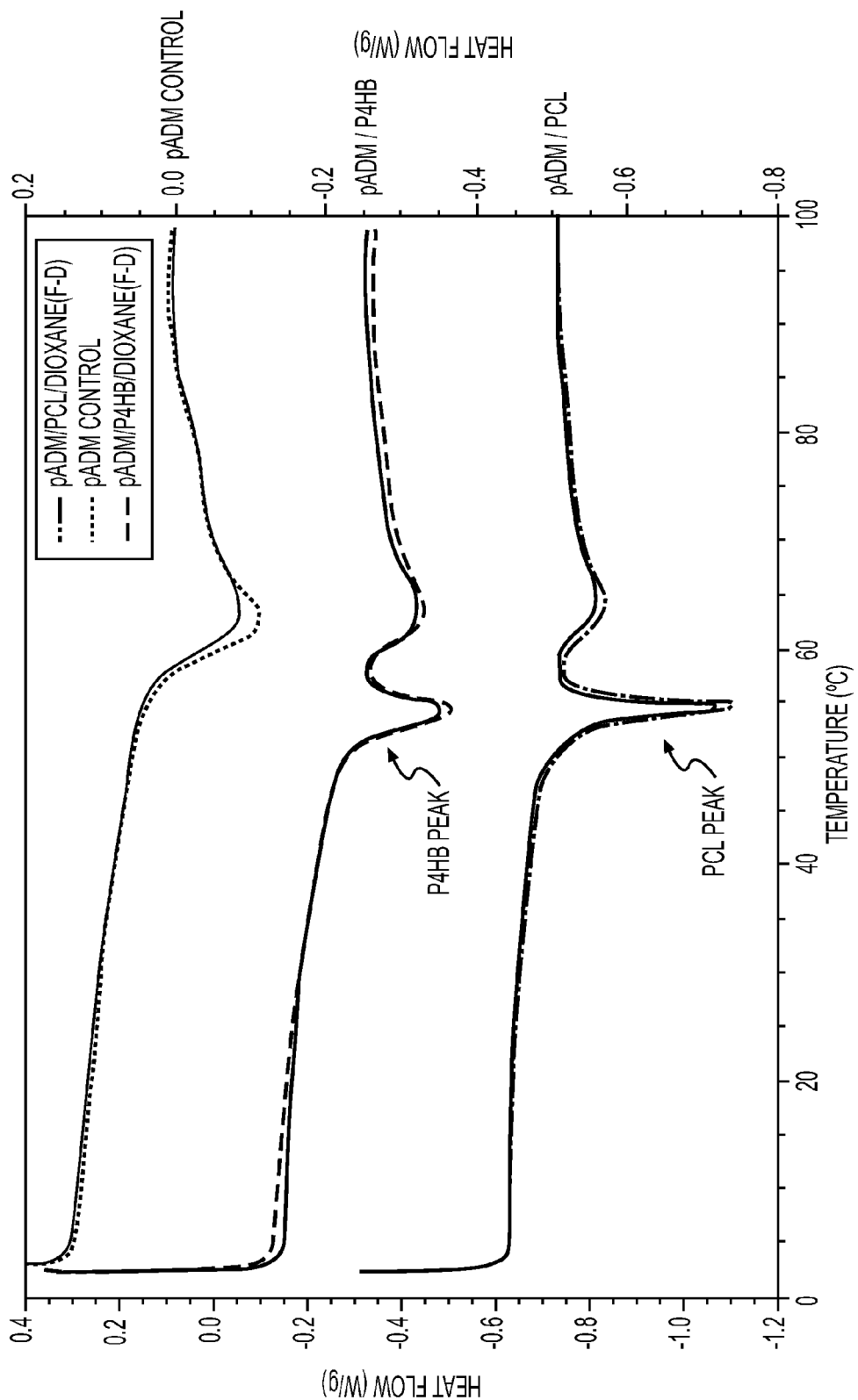
FIG. 4 is a graph of DSC data of pADM in presence of polymers, according to Example 2.
Figure 5B:
FIG. 5B is a hematoxylin and eosin stained four week sub-dermal explant comprising pADM and P4HB under 100× magnification, according to the process described in Example 2.
Figure 5D:
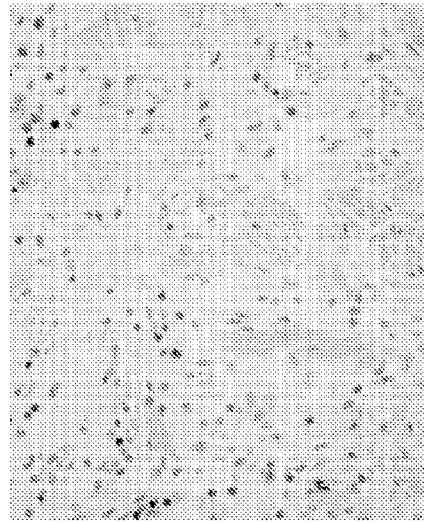
FIG. 5D is a hematoxylin and eosin stained four week sub-dermal explant comprising pADM and P4HB under 400× magnification, according to the process described in Example 2.
Figure 5A:
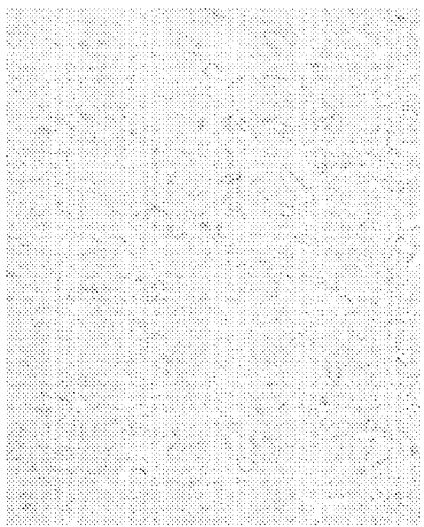
FIG. 5A is a hematoxylin and eosin stained four week sub-dermal explant comprising poly-4-hydroxybutyrate (P4HB) under 100× magnification, according to the process described in Example 2.
Figure 5C:
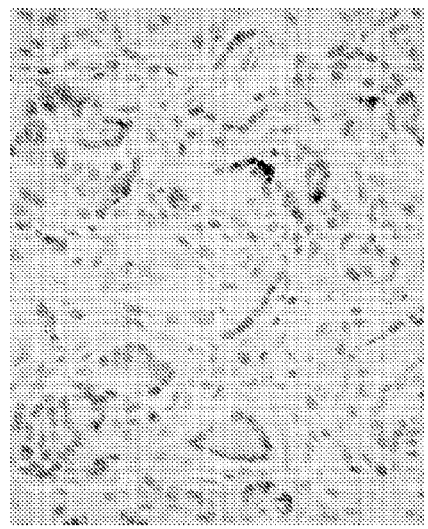
FIG. 5C is a hematoxylin and eosin stained four week sub-dermal explant comprising P4HB under 400× magnification, according to the process described in Example 2.
Figure 6A:
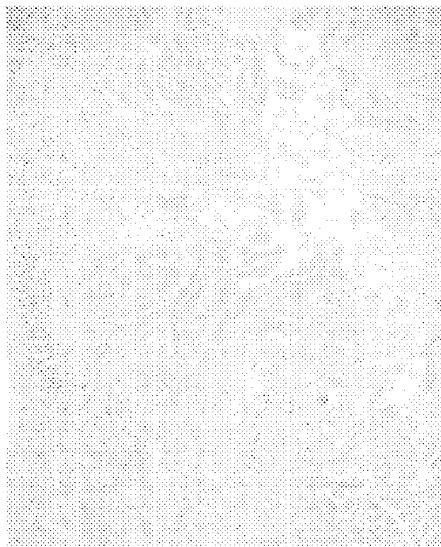
FIG. 6A is a hematoxylin and eosin stained twelve week sub-dermal explant comprising P4HB under 100× magnification, according to the process described in Example 2.
Figure 6B:
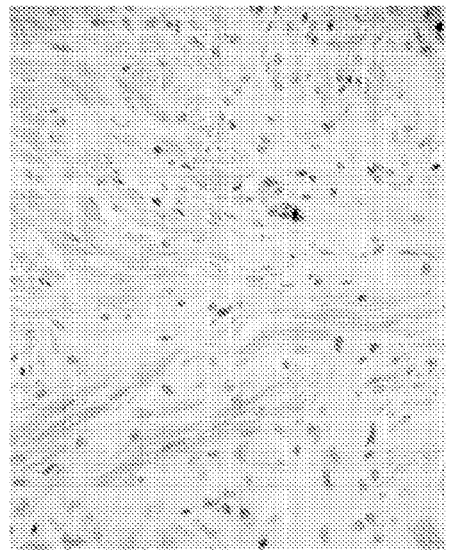
FIG. 6B is a hematoxylin and eosin stained twelve week sub-dermal explant comprising pADM and P4HB under 100× magnification, according to the process described in Example 2.
Figure 6C:
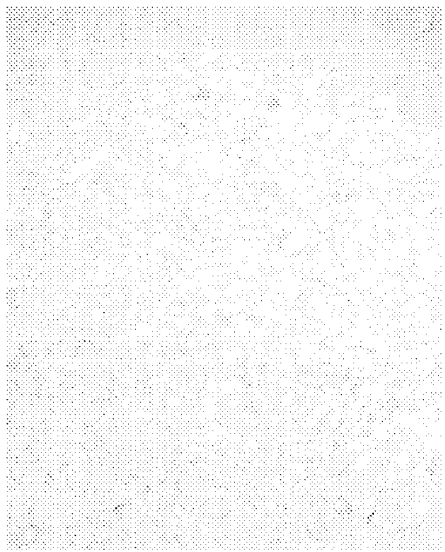
FIG. 6C is a hematoxylin and eosin stained twelve week sub-dermal explant comprising P4HB under 400× magnification, according to the process described in Example 2.
Figure 6D:
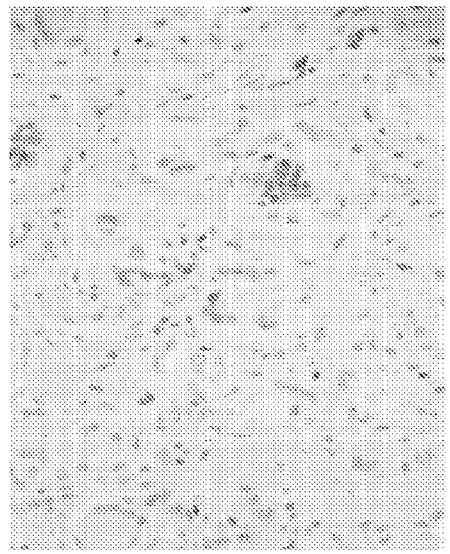
FIG. 6D is a hematoxylin and eosin stained twelve week sub-dermal explant comprising pADM and P4HB under 400× magnification, according to the process described in Example 2.
Figure 7A:
FIG. 7A is a hematoxylin and eosin stained four week sub-dermal explant comprising polycaprolactone (PCL) under 100× magnification, according to the process described in Example 2.
Figure 7B:
FIG. 7B is a hematoxylin and eosin stained four week sub-dermal explant comprising pADM and PCL under 100× magnification, according to the process described in Example 2.
Figure 7C:
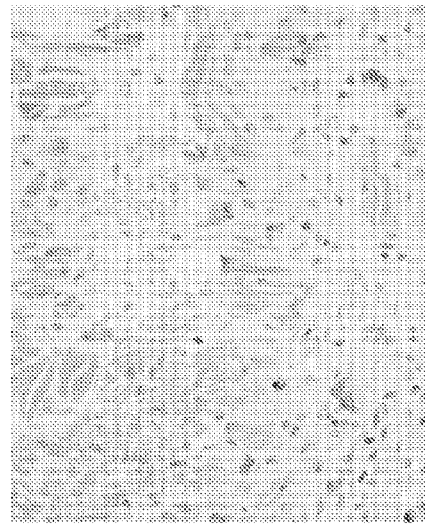
FIG. 7C is a hematoxylin and eosin stained four week sub-dermal explant comprising PCL under 400× magnification, according to the process described in Example 2.
Figure 7D:
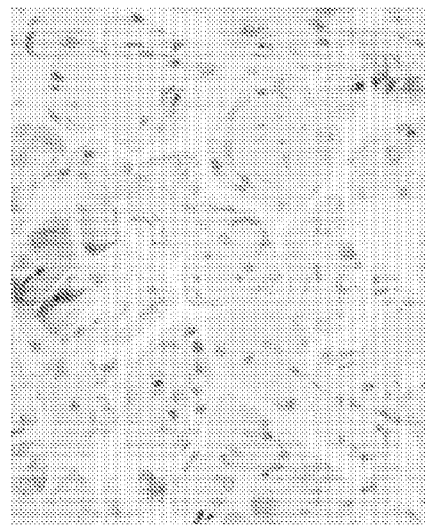
FIG. 7D is a hematoxylin and eosin stained four week sub-dermal explant comprising pADM and PCL under 400× magnification, according to the process described in Example 2.
Figure 8A:
FIG. 8A is a hematoxylin and eosin stained twelve week sub-dermal explant comprising PCL under 100× magnification, according to the process described in Example 2.
Figure 8B:
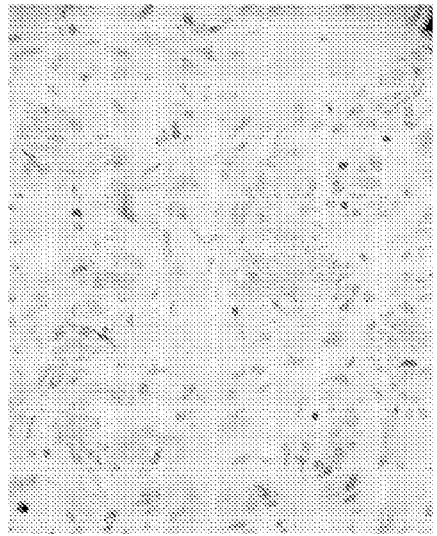
FIG. 8B is a hematoxylin and eosin stained twelve week sub-dermal explant comprising pADM and PCL under 100× magnification, according to the process described in Example 2.
Figure 8C:
FIG. 8C is a hematoxylin and eosin stained twelve week sub-dermal explant comprising PCL under 400× magnification, according to the process described in Example 2.
Figure 8D:
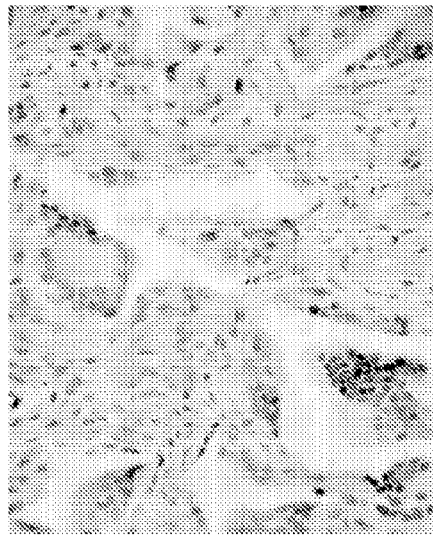
FIG. 8D is a hematoxylin and eosin stained twelve week sub-dermal explant comprising pADM and PCL under 400× magnification, according to the process described in Example 2.
Figure 9A:
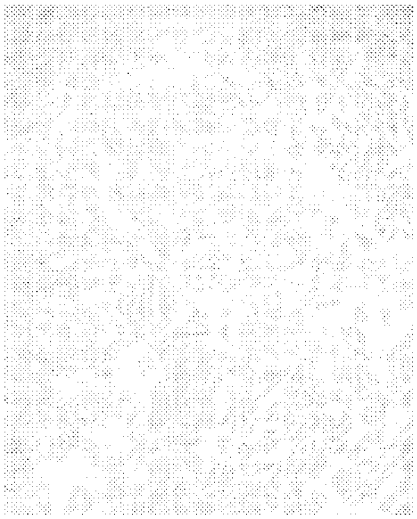
FIG. 9A is a hematoxylin and eosin stained four week sub-dermal explant comprising hyaluronic acid benzyl ester (BHA) under 100× magnification, according to the process described in Example 2.
Figure 9B:
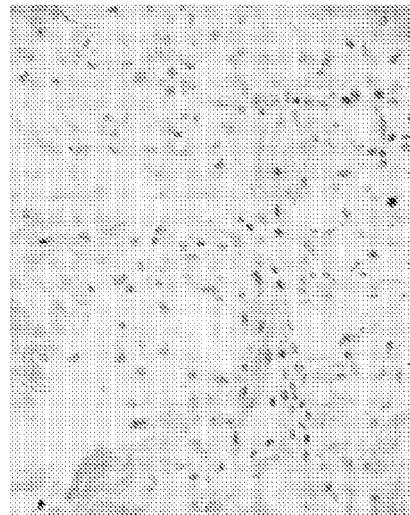
FIG. 9B is a hematoxylin and eosin stained four week sub-dermal explant comprising pADM and BHA under 100× magnification, according to the process described in Example 2.
Figure 9C:
FIG. 9C is a hematoxylin and eosin stained four week sub-dermal explant comprising BHA under 400× magnification, according to the process described in Example 2.
Figure 9D:
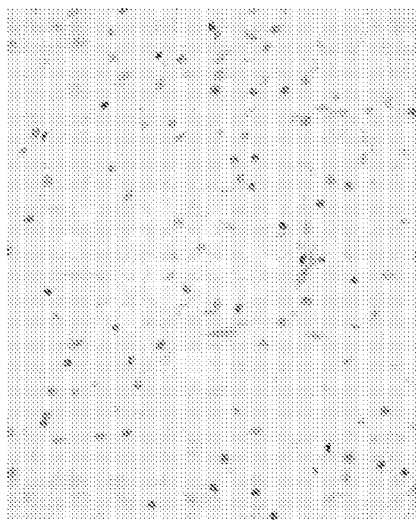
FIG. 9D is a hematoxylin and eosin stained four week sub-dermal explant comprising pADM and BHA under 400× magnification, according to the process described in Example 2.
Figure 10A:
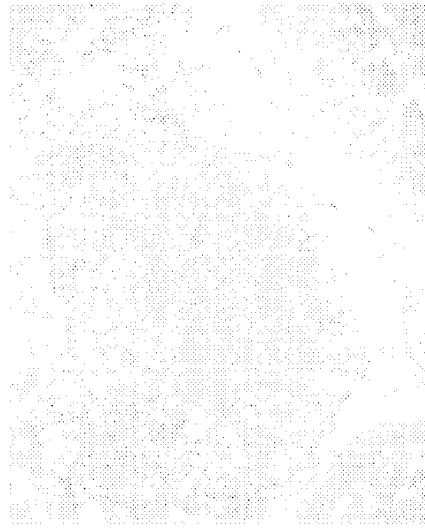
FIG. 10A is a hematoxylin and eosin stained twelve week sub-dermal explant comprising BHA under 100× magnification, according to the process described in Example 2.
Figure 10B:
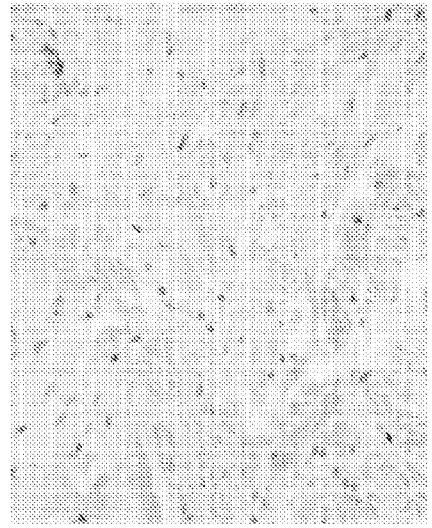
FIG. 10B is a hematoxylin and eosin stained twelve week sub-dermal explant comprising pADM and BHA explant under 100× magnification, according to the process described in Example 2.
Figure 10C:
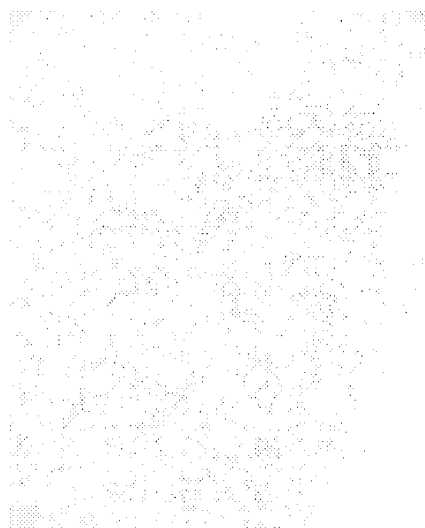
FIG. 10C is a hematoxylin and eosin stained twelve week sub-dermal explant comprising BHA under 400× magnification, according to the process described in Example 2.
Figure 10D:
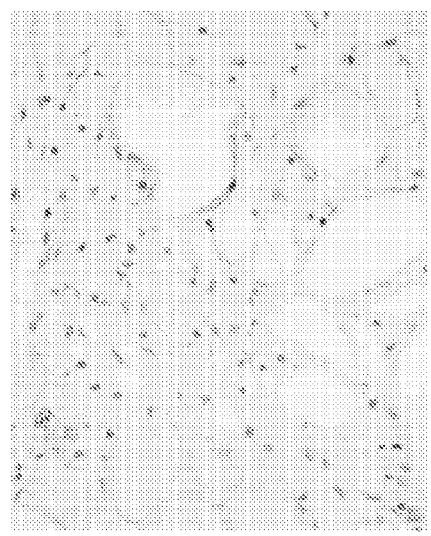
FIG. 10D is a hematoxylin and eosin stained twelve week sub-dermal explant comprising pADM and BHA under 400× magnification, according to the process described in Example 2.

Similarly, pADMs were treated with different polymers, for example, poly-4-hydroxybutyrate in dioxane or NMP and polycaprolactone in dioxane or NMP, and evaluated tissue matrix integrity by DSC. FIG. 4 is a graph of DSC data of pADM in presence of polymers, according to Example 2. DSC analysis (FIG. 4) showed that thermograms of polymer and pADM were additive.

Histological Evaluation

The effect of implantation of pADM was tested in the presence of poly-4-hydroxybutyrate (P4HB) in a sub-dermal immune-competent rat model. Immune-competent rats were implanted with pADM/P4HB tissue scaffold or P4HB polymer scaffold. This model allowed for the determination of cellular and immunological responses to the implanted test materials. Test materials were implanted in a sub-dermal position through a small incision on the dorsal surface of immune-competent rats (*Rattus norvegicus*; Lewis Rat). Four weeks (FIGS. 5A-D) and 12 weeks (FIGS. 6A-D) after implantation, explants were collected and washed with PBS and were fixated in 10% formalin. Fixed tissue was embedded in paraffin and sections of tissue matrix samples were stained with hematoxylin and eosin (H&E) using standard procedures. D. C. Sheehan and B. B. Hrapchak, Theory and Practice of Histotechnology, 2$^{nd}$ edn., Columbus, Ohio, Battelle Press (1987). Samples were then observed under microscope at 100× magnification (FIGS. 5A-B and 6A-B) and 400× magnification (FIGS. 5C-D and 6C-D). Histology analysis of the explants (FIGS. 5A-D and 6A-D) showed that P4HB in the presence of pADM had an attenuated inflammatory response compared to explants of P4HB alone.

FIGS. 7A-D and 8A-D show histological evaluation of 4 and 12 week polycaprolactone explants. The effect of implantation of pADM was tested in the presence of polycaprolactone (PCL) in a sub-dermal immune-competent rat model. Immune-competent rats were implanted with pADM/PCL scaffold or PCL polymer scaffold. Four (FIGS. 7A-D) and 12 weeks (FIGS. 8A-D) after implantation, explants were collected and processed for histological evaluation, as described above. Samples were then observed under microscope at 100× magnification (FIGS. 7A-B and 8A-B) and 400× magnification (FIGS. 7C-D and 8C-D). Histology analysis of the explants (FIGS. 7A-D and 8A-D) showed that PCL in the presence of pADM had an attenuated inflammatory response compared to explants of PCL alone.

FIGS. 9A-D and 10A-D show histological evaluation of 4 and 12 week hyaluronic acid benzyl ester (BHA) explants. The effect of implantation of pADM was tested in the presence of BHA in a sub-dermal immune-competent rat model. Immune-competent rats were implanted with pADM/BHA scaffold or BHA polymer scaffold. Four (FIGS. 9A-D) and 12 weeks (FIGS. 10A-D) after implantation, explants were collected and processed for histological evaluation, as described above. Samples were then observed under microscope at 100× magnification (FIGS. 9A-B and 10A-B) and 400× magnification (FIGS. 9C-D and 10C-D). Histology analysis of the explants (FIGS. 9A-D and 10A-D) showed that BHA in the presence of pADM had an attenuated inflammatory response compared to explants of BHA alone.

Figure 11B:
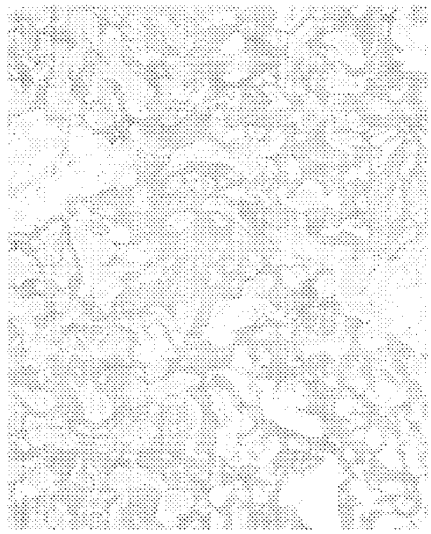
FIG. 11B is a hematoxylin and eosin stained eight week explant comprising chitosan and pADM under 100× magnification, according to the process described in Example 2.
Figure 11D:
FIG. 11D is a hematoxylin and eosin stained eight week explant comprising chitosan and pADM under 400× magnification, according to the process described in Example 2.
Figure 11A:
FIG. 11A is a hematoxylin and eosin stained four week explant comprising chitosan and pADM under 100× magnification, according to the process described in Example 2.
Figure 11C:
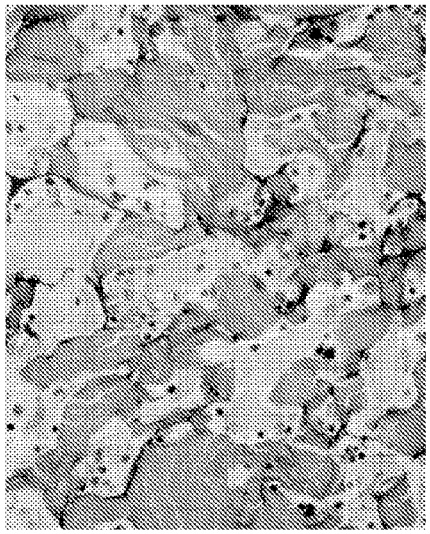
FIG. 11C is a hematoxylin and eosin stained four week explant comprising chitosan and pADM under 400× magnification, according to the process described in Example 2.

FIGS. 11A-D show histological evaluation of 4 and 8 week chitosan/pADM explants. The effect of implantation of pADM was tested in the presence of chitosan in a sub-dermal immune-competent rat model. Immune-competent rats were implanted with pADM/chitosan scaffold. Four (FIGS. 11A, C) and 8 weeks (FIGS. 11B, D) after implantation, explants were collected and processed for histological evaluation, as described above. Samples were then observed under microscope at 100× magnification (FIGS. 11A-B) and 400× magnification (FIGS. 11C-D). The results showed that there was a regenerative tissue response, as demonstrated by the presence of fibroblast-like cells and blood vessels.

The capacity to mold and shape regenerative tissue matrices into stable three-dimensional structures, as described above, will allow for the development of novel products that can be used over a broad range of regenerative medical applications. Each of these scaffold materials may impart different properties upon the final product allowing for the manipulations of in vivo turnover/persistence, biomechanical properties and overall biological response. In addition, as shown above, the regenerative tissue matrix component reduces/attenuates the overall inflammatory response to the scaffold materials.

The invention claimed is:
1. A tissue scaffold, comprising:
an acellular tissue matrix (ATM) comprising a group of ATM particulates; and
a polymer;

wherein the ATM particulates are encased in the polymer to form a stable three-dimensional tissue scaffold for tissue regeneration, and the tissue scaffold has a reduced immunological or inflammatory response when implanted in a human than the polymer alone; and the polymer has been dissolved in a solvent to form a polymer solution, the ATM particulates have been submerged in and mixed with the polymer solution to form a moldable mixture, and the moldable mixture has been dried to produce a polymer scaffold completely surrounding the ATM particulates.

2. The tissue scaffold of claim 1, wherein the polymer comprises a synthetic polymer.

3. The tissue scaffold of claim 1, wherein the polymer comprises a polycaprolactone.

4. The tissue scaffold of claim 1, wherein the polymer is a poly4-hydroxybutyrate.

5. The tissue scaffold of claim 1, wherein the polymer comprises a benzyl ester derivative of hyaluronic acid.

6. The tissue scaffold of claim 1, wherein the polymer comprises chitosan.

7. The tissue scaffold of claim 1, wherein the ATM comprises a dermal ATM.

8. The tissue scaffold of claim 7, wherein the dermal ATM is a human tissue matrix.

9. The tissue scaffold of claim 7, wherein the dermal ATM is a porcine tissue matrix.

10. The tissue scaffold of claim 1, wherein the ATM is a cartilage tissue matrix.

11. The tissue scaffold of claim 10, wherein the cartilage tissue matrix comprises a human cartilage.

12. The tissue scaffold of claim 10, wherein the cartilage tissue matrix comprises a porcine cartilage.

13. The tissue scaffold of claim 1, wherein the ATM is a bone tissue matrix.

14. The tissue scaffold of claim 13, wherein the bone tissue matrix is derived from human bone.

15. The tissue scaffold of claim 13, wherein the bone tissue matrix is derived from porcine bone.

16. The tissue scaffold of claim 1, wherein the ATM includes tissue matrices derived from two or more different types of tissues.

17. The tissue scaffold of claim 16, wherein the two or more different types of tissues include cartilage and demineralized bone.

18. The tissue scaffold of claim 1, wherein the solvent includes at least one of dioxane, N-methyl-2-pyrrolidone, DMSO, and acetic acid.

19. The tissue scaffold of claim 1, wherein drying includes a drying process selected from at least one of freeze drying, air drying, heated drying, drying in an argon or nitrogen atmosphere, and vacuum assisted drying.

20. A tissue scaffold, comprising:
an acellular tissue matrix (ATM) comprising a group of ATM particulates; and
a polymer;
wherein the ATM particulates are encased in the polymer to form a stable three-dimensional tissue scaffold for tissue regeneration, and the tissue scaffold has a reduced immunological or inflammatory response when implanted in a human than the polymer alone; and
wherein the ATM particulates have been mixed with a polymer solution to form a moldable mixture, and the moldable mixture has been dried to produce the stable three-dimensional tissue scaffold.

21. The tissue scaffold of claim 20, wherein the ATM comprises a dermal ATM.

22. The tissue scaffold of claim 21, wherein the dermal ATM is a human tissue matrix.

23. The tissue scaffold of claim 21, wherein the dermal ATM is a porcine tissue matrix.

* * * * *